(12) United States Patent
Soin et al.

(10) Patent No.: US 10,478,831 B1
(45) Date of Patent: Nov. 19, 2019

(54) BIOLUMINESCENT TORNADO MAKER SYSTEM

(71) Applicants: Aviraj G. Soin, Dayton, OH (US); Dhilen N. Soin, Dayton, OH (US)

(72) Inventors: Aviraj G. Soin, Dayton, OH (US); Dhilen N. Soin, Dayton, OH (US)

(*) Notice: Subject to any disclaimer, the term of this patent is extended or adjusted under 35 U.S.C. 154(b) by 0 days.

(21) Appl. No.: 16/414,806

(22) Filed: May 17, 2019

(51) Int. Cl.
- *A01K 67/027* (2006.01)
- *B04C 3/00* (2006.01)
- *F21K 2/00* (2006.01)
- *F21W 121/00* (2006.01)

(52) U.S. Cl.
CPC .............. *B04C 3/00* (2013.01); *F21K 2/00* (2013.01); *B04C 2003/006* (2013.01); *F21W 2121/00* (2013.01)

(58) Field of Classification Search
CPC ........ B04C 3/00; B04C 2003/006; F21K 2/00
See application file for complete search history.

(56) References Cited

U.S. PATENT DOCUMENTS

| | | | |
|---|---|---|---|
| 4,490,931 A | 1/1985 | Fleemin | |
| 5,272,604 A * | 12/1993 | Lin | B04C 5/00 362/101 |
| 6,006,461 A | 12/1999 | Snyder | |
| 6,183,336 B1 | 2/2001 | Coleman | |
| 6,247,995 B1 * | 6/2001 | Bryan | A23G 3/366 124/74 |
| 6,295,749 B1 | 10/2001 | Lin | |
| 6,416,197 B1 | 7/2002 | Chang | |
| 6,877,883 B2 * | 4/2005 | Lau Ting Yup | G09F 13/24 362/101 |
| 6,990,762 B1 | 1/2006 | Muday | |
| 7,905,728 B2 | 3/2011 | Piontek | |
| 2006/0053505 A1 * | 3/2006 | Bryan | A23G 3/366 800/20 |
| 2014/0334249 A1 | 11/2014 | Radow | |

* cited by examiner

*Primary Examiner* — Anabel Ton
(74) *Attorney, Agent, or Firm* — Neustel Law Offices

(57) ABSTRACT

A bioluminescent tornado maker system for creating a pleasing, glow-in-the-dark tornado. The bioluminescent tornado maker system generally includes a base that supports a transparent vessel having a liquid within it. The liquid may be salt water, and may contain bioluminescent organisms, such as dinoflagellates. An impeller in the base in contact with the liquid causes a rotational flow of the liquid, creating a visible vortex and also a mechanical disturbance that causes the bioluminescent organisms to emit a visible light, resulting in a glow-in-the-dark tornado.

20 Claims, 11 Drawing Sheets

BIOLUMINESCENT TORNADO MAKER SYSTEM

CROSS REFERENCE TO RELATED APPLICATIONS

Not applicable to this application.

STATEMENT REGARDING FEDERALLY SPONSORED RESEARCH OR DEVELOPMENT

Not applicable to this application.

BACKGROUND

Field

Example embodiments in general relate to a bioluminescent tornado maker system for creating a visually pleasing vortex in a liquid that exhibits bioluminescence.

Related Art

Any discussion of the related art throughout the specification should in no way be considered as an admission that such related art is widely known or forms part of common general knowledge in the field.

Toy tornado makers have been in use for some time, with varying devices employed to make them more visually interesting.

However, such toys in the past have depended on fluids of differing specific gravities, electrical lights, and "passive" visible objects within the liquid medium to create various visual effects.

SUMMARY

An example embodiment is directed to a bioluminescent tornado maker system. The bioluminescent tornado maker system includes a transparent vessel and a liquid disposed within the transparent vessel, wherein the liquid comprises salt water and bioluminescent organisms, for example, dinoflagellates. The embodiment also includes an impeller in contact with the liquid such that a rotation of the impeller causes a flow of the liquid, wherein the flow of the liquid creates a disturbance that causes the bioluminescent organisms to emit a visible light.

In another example embodiment of the bioluminescent tornado maker the flow of the liquid is a rotational flow created by the impeller. The rotational flow of the liquid can create a visible vortex within the transparent vessel. Further, the system may also comprise a stable base that is sealingly coupled to the transparent vessel, wherein the impeller is mounted in the base. However, in another embodiment, an electric motor may be mounted within the base, the electric motor coupled to the impeller such that the electric motor rotates the impeller when energized. The electric motor may be energized for only a limited time by a time-delay circuit, for example, about thirty seconds, to prevent damage to the bioluminescent organisms.

Another example embodiment may further comprise an air pump coupled to the transparent vessel, wherein the air pump creates air bubbles in the liquid. The air bubbles may be present in, and part of, the visible vortex within the transparent vessel.

The toy tornado maker may be battery powered—that is, both the air pump and the electric motor may be powered by batteries, under the control of circuitry within or mounted on the base. Other embodiments, such as those with a power supply that uses household current, are also possible. The tornado maker system may, for example, be powered by four AA batteries, which may be accessed or changed by opening a battery access door in the bottom of the base.

As mentioned above, the transparent vessel in some example embodiments may be sealingly coupled or connected to the base, and the top or upper surface of the base may serve as the bottom of the vessel to contain the liquid medium within the vessel. Due to its transparency, the vessel enables users to see the "tornado" generated by the toy, and to also see it glowing when used in the dark.

There has thus been outlined, rather broadly, some of the embodiments of the bioluminescent tornado maker system in order that the detailed description thereof may be better understood, and in order that the present contribution to the art may be better appreciated. There are additional embodiments of the bioluminescent tornado maker system that will be described hereinafter and that will form the subject matter of the claims appended hereto. In this respect, before explaining at least one embodiment of the bioluminescent tornado maker system in detail, it is to be understood that the bioluminescent tornado maker system is not limited in its application to the details of construction or to the arrangements of the components set forth in the following description or illustrated in the drawings.

The bioluminescent tornado maker system is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Example embodiments will become more fully understood from the detailed description given herein below and the accompanying drawings, wherein like elements are represented by like reference characters, which are given by way of illustration only and thus are not limitative of the example embodiments herein.

DETAILED DESCRIPTION

A. Overview

Figure 1:
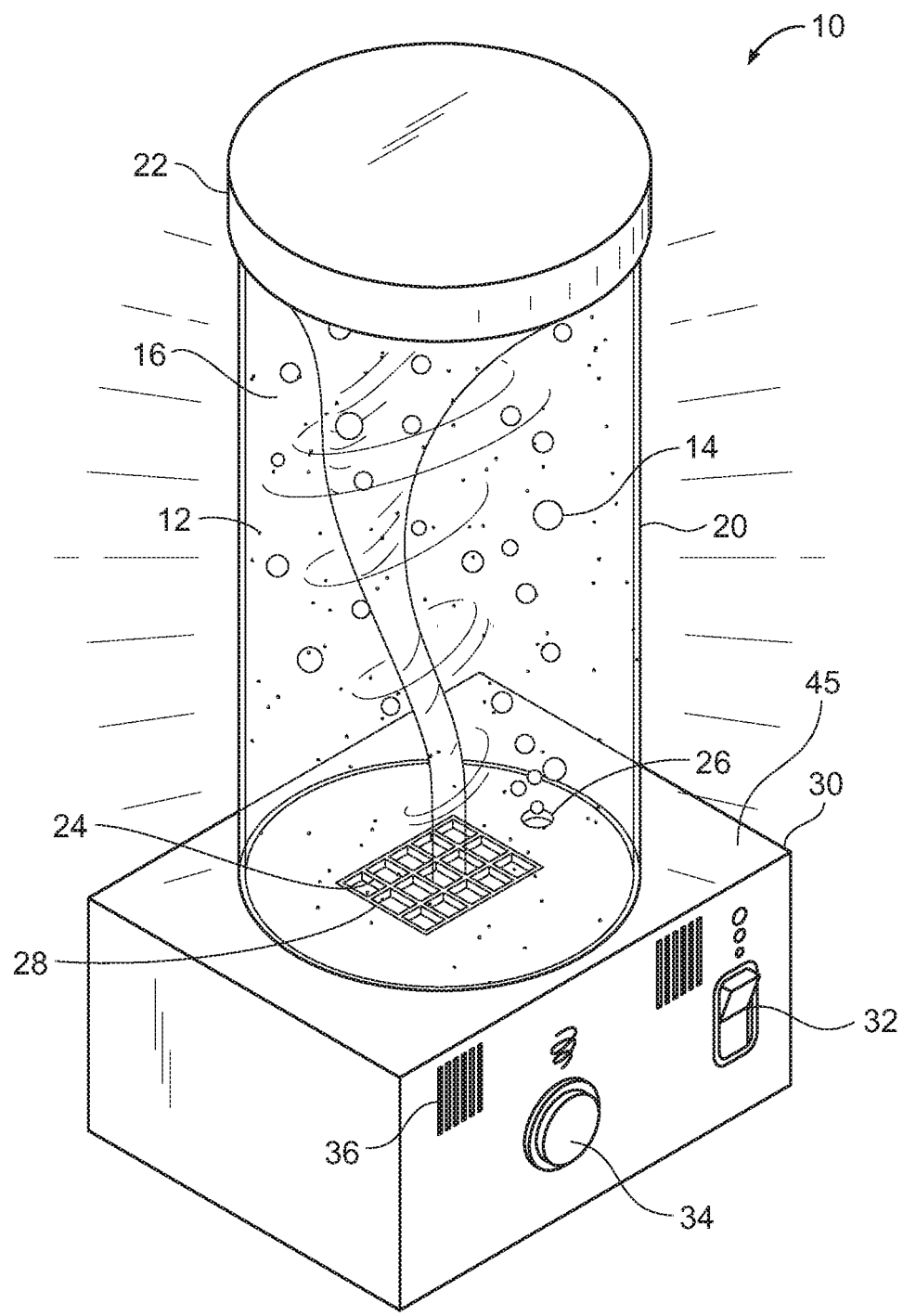
FIG. 1 is a perspective view of a bioluminescent tornado maker system in accordance with an example embodiment.

An example bioluminescent tornado maker system 10 generally comprises a transparent vessel 20 and a liquid 16 disposed within the transparent vessel, wherein the liquid may include salt water and bioluminescent organisms 12. The embodiment also includes an impeller 41 in contact with the liquid 16 such that a rotation of the impeller 41 causes a flow of the liquid 16, wherein the flow of the liquid 16 creates a disturbance that causes the bioluminescent organisms 12 to emit a visible light. In the bioluminescent tornado maker 10, the flow of the liquid 16 is a rotational flow, and it can create a pleasing and interesting visible vortex within the transparent vessel 20.

The system may also comprise a base 30 that is sealingly coupled to the transparent vessel 20. More specifically, the base 30 can support the transparent vessel 20, as well as contain components useful for the operation of the tornado maker, such as circuitry, a motor, and a pump, as explained below. The impeller 41 may be mounted in the base 30. However, in another embodiment, an electric motor 40 may be mounted within the base 30, the electric motor 40 coupled to the impeller 41 such that the electric motor 40 rotates the impeller 41 when energized. The electric motor 40 may be energized for only a limited time by a time-delay circuit 82, to prevent damage to the bioluminescent organisms 12.

The tornado maker may also have an air pump 42 coupled to the transparent vessel 20, wherein the air pump 42 creates air bubbles 14 in the liquid 16. The air bubbles 14 may be present in, and part of, the visible vortex within the transparent vessel 20.

The toy 10 may be battery powered—that is, both the air pump 42 and the electric motor 40 may be powered by batteries 80, under the control of circuitry within or mounted on the base 30. Other embodiments, such as those with a power supply that uses household current, are also possible. The circuitry and components may include a switch 32 coupled to the air pump 42, and a switch 34 coupled, directly or indirectly, to the electric motor which drives the impeller. As mentioned briefly above, the switch 34 for the motor/impeller may be used to simply trigger or start a delay circuit 82, which will provide power to the impeller 41 for a period of time, such as thirty seconds, and then automatically shut off the power.

When a user activates the tornado maker 10, especially in the dark or at night, the impeller 41 will create a vortex that is visible to the users, and the flow of liquid and its contact with the impeller 41 will create a mechanical disturbance that causes the bioluminescent organisms 12 to emit visible light, making the toy glow. In addition, if the pump 42 is activated, the liquid 16 and the vortex will also have bubbles 14, resulting in a pleasing visual effect.

B. Base

Figure 2:
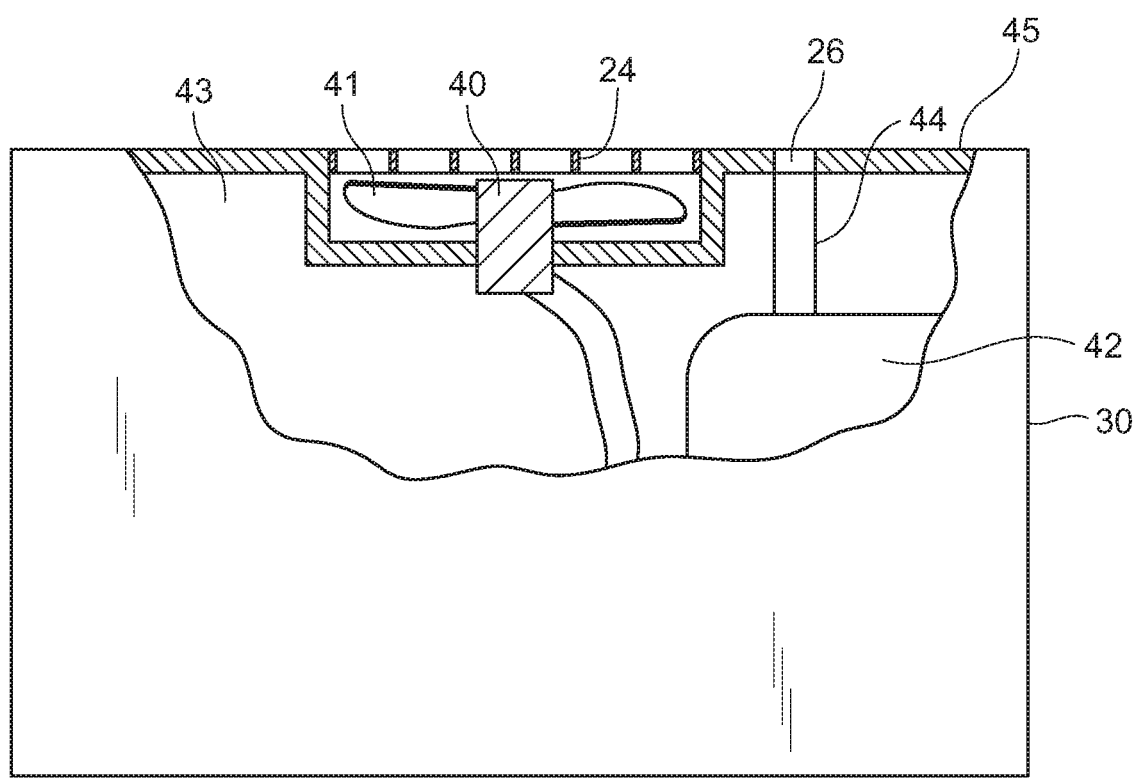
FIG. 2 is a partial sectional view of a bioluminescent tornado maker system in accordance with an example embodiment.
Figure 3:
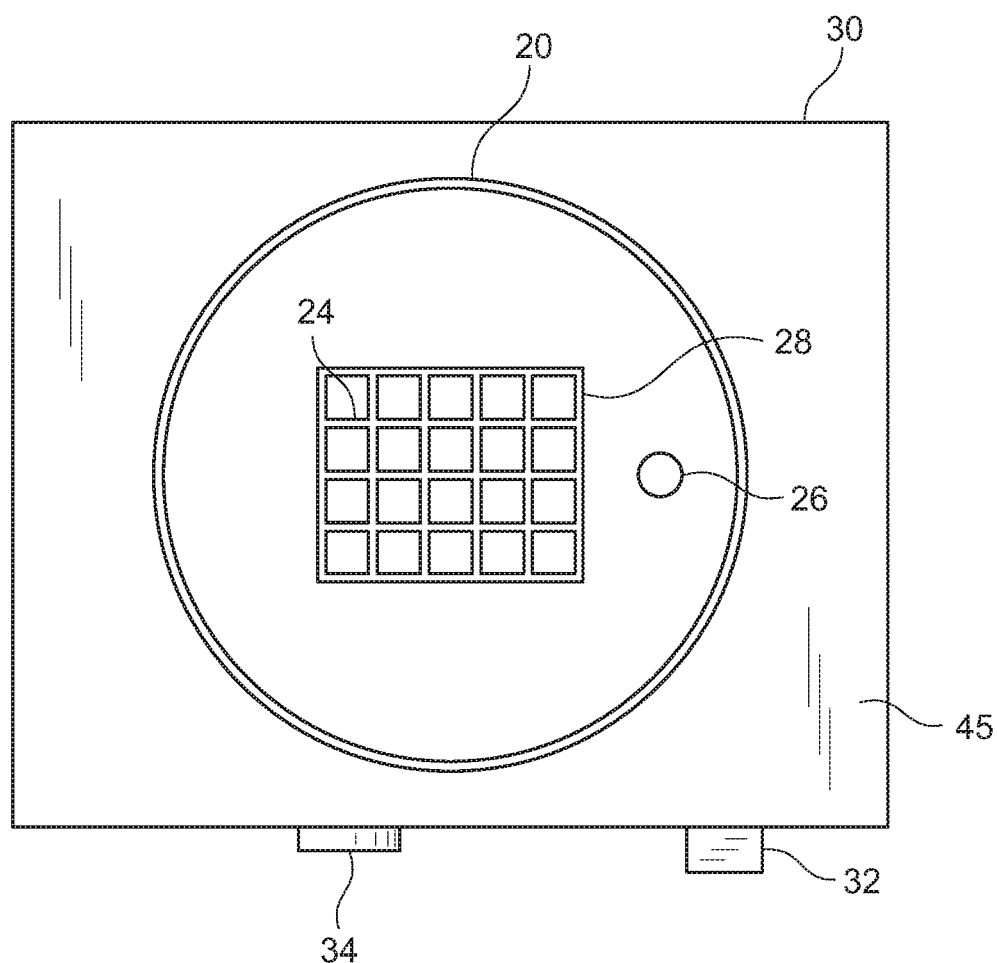
FIG. 3 is a top view of a bioluminescent tornado maker system in accordance with an example embodiment.
Figure 4:
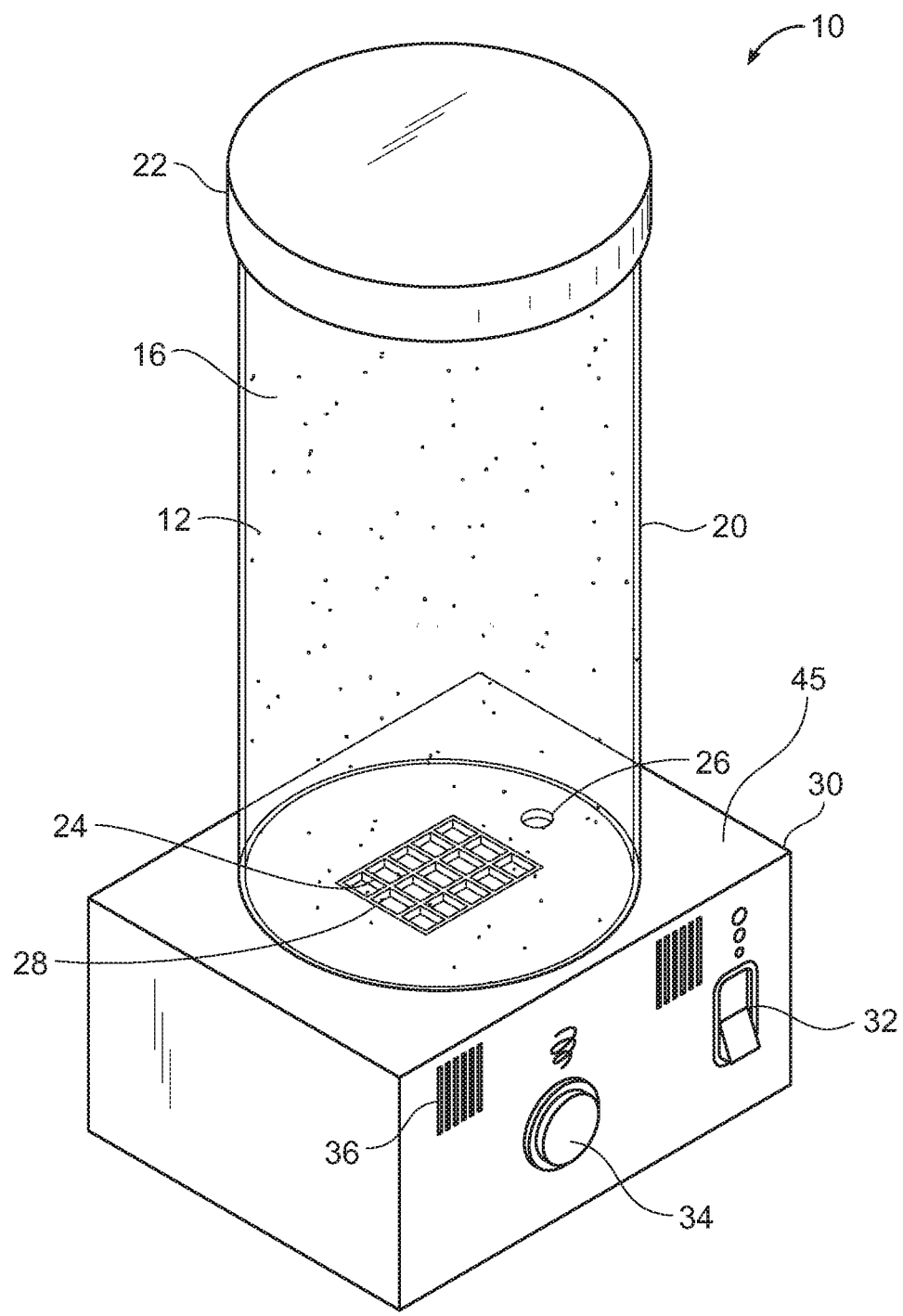
FIG. 4 is another perspective view of a bioluminescent tornado maker system in accordance with an example embodiment.

As best shown in FIGS. 1 and 2, an example tornado maker system may comprise a base 30 that is sealingly coupled to the transparent vessel 20, such that the base 30 provides support for the vessel 20, and also contains circuitry and components of the system. More specifically, the base 30 may include switches 32 and 34 for activating the air pump 42 and the electric motor 40, respectively. In addition, the air pump 42 and the motor 40 may be mounted or contained within the base 30, as shown. The base 30 may also include an upper surface 45 which keeps the liquid from entering the base, and also serves as the bottom of the transparent vessel 20, which may be sealingly connected to the base 30. To keep the components within the base dry, the base 30 may include an inner chamber 43, which is separated from the impeller 41 and/or the motor 40.

The base 30 may include a number of air vents 36 that permit air to enter the chamber 43 of the base, which can thus flow to the air pump 42 to create bubbles 14. The air pump 42 may pump air to the liquid 16 via tube 44, and the air may exit orifice 26 in the upper surface 45 of the base 30. The tube may be sealed with a rubber O-ring (not shown) to prevent leakage of any liquid into the chamber 43. The base 30 may also have an opening 28 that allows water to enter and come in contact with the impeller 41. The opening 28 may be covered by an open grate 24, which allows liquid to come in contact with the impeller 41, but prevents any objects from hitting the impeller, and also provide nominal protection for the bioluminescent organisms 12.

Figure 9:
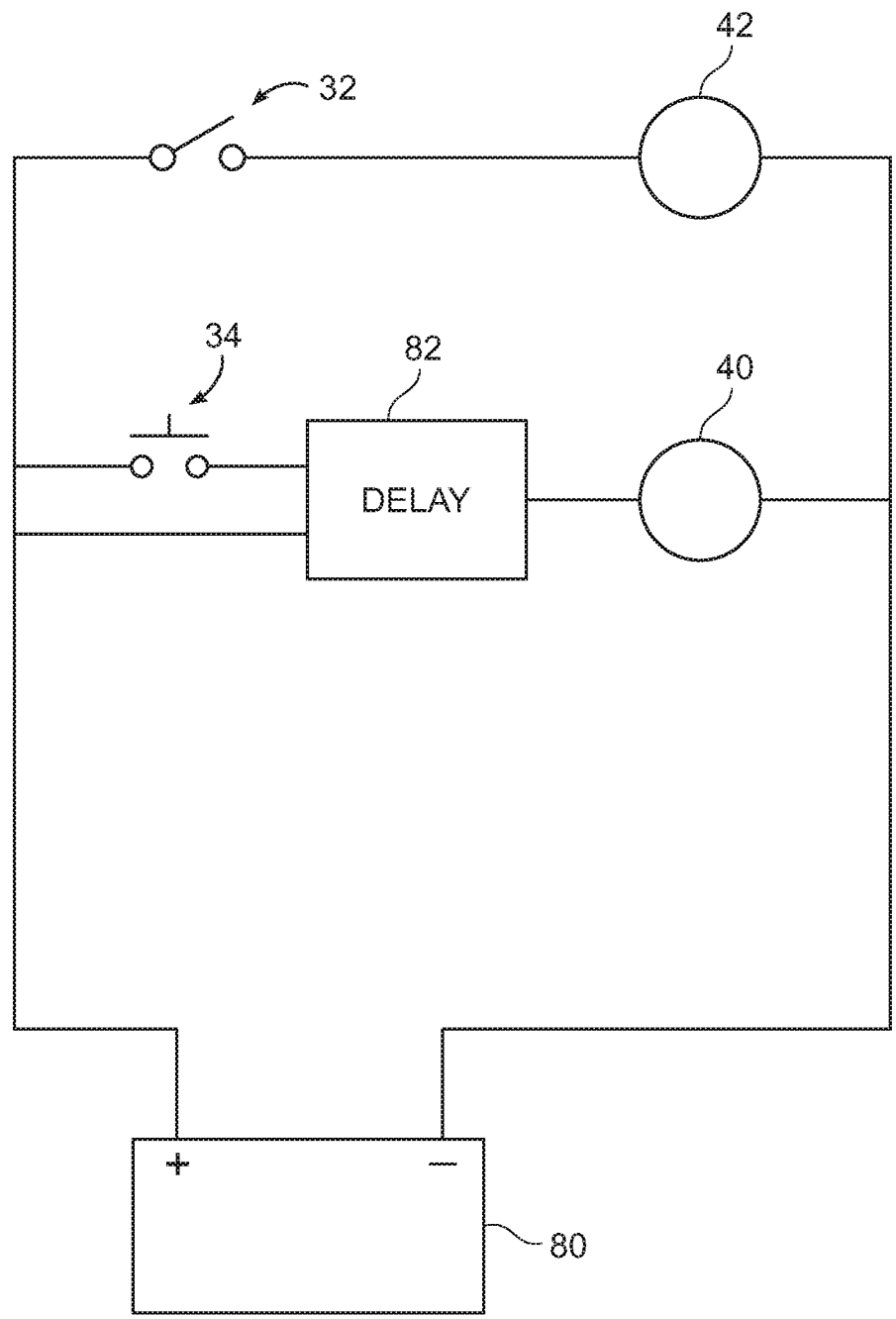
FIG. 9 is a schematic diagram of a bioluminescent tornado maker system in accordance with an example embodiment.

The base 30 may also include an electric motor 40, coupled to an impeller 41. The impeller 41 may be in the form of a paddle or fan, to impart a rotational flow or movement to the liquid 16 within the transparent vessel 20. If the impeller 41 is in the form of a fan, the fan or impeller blades may have rounded edges, and no sharp corners, and may be tilted about 30° to help the liquid flow and create a vortex when turned on. The impeller may be directly or magnetically coupled to the motor 40, such that the electric motor 40 rotates the impeller 41 when energized. The electric motor 40 may be energized for only a limited time by a time-delay circuit 82, to prevent damage to the bioluminescent organisms 12. The time-delay circuit 82 is shown in FIG. 9, along with a general electrical diagram of the system. As shown, rather than being directly connected, switch 34 simply provides an input to circuit 82.

Circuit 82, which may be a discrete integrated circuit timer, can then provide a temporary power output to motor 40, even after switch 34 is released. Although other embodiments are possible, as shown in FIG. 9, the pump switch 32 may be a continuous, on-off switch or rocker switch, that remains closed once activated, for creating the bubbles 14. In contrast, "tornado" switch 34 may be a push-button switch that only closes temporarily when it is pushed.

Figure 10:
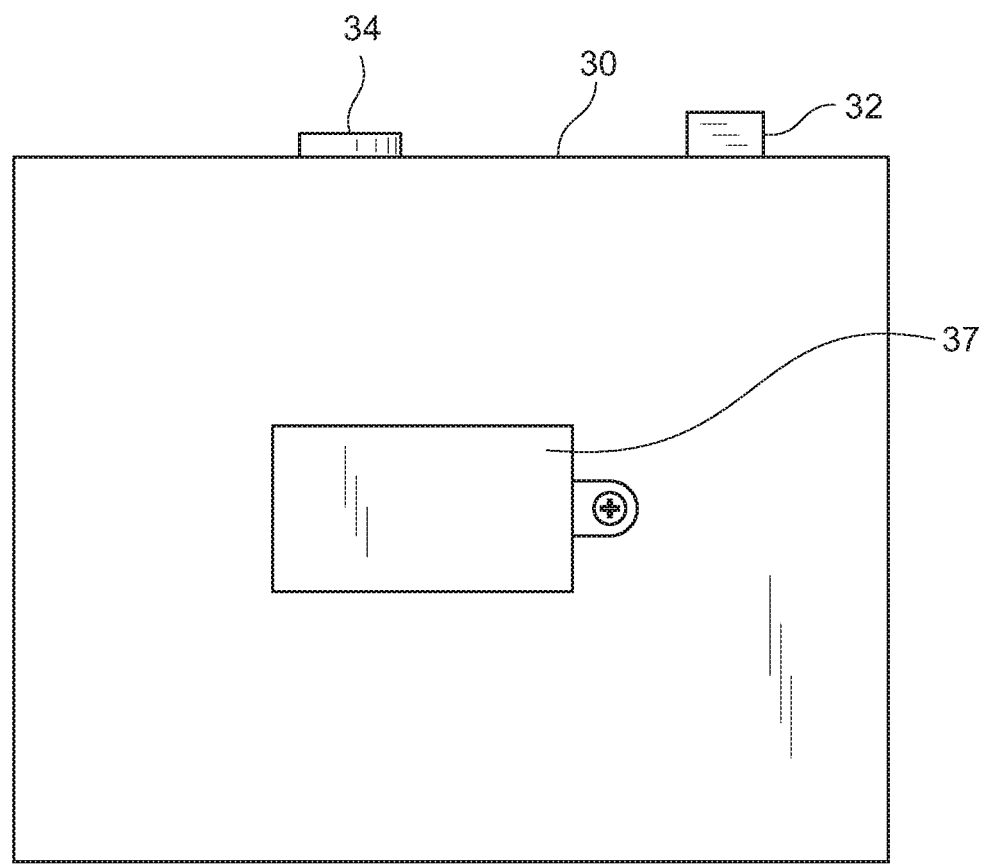
FIG. 10 is a bottom view of a bioluminescent tornado maker system in accordance with an example embodiment.
Figure 11:
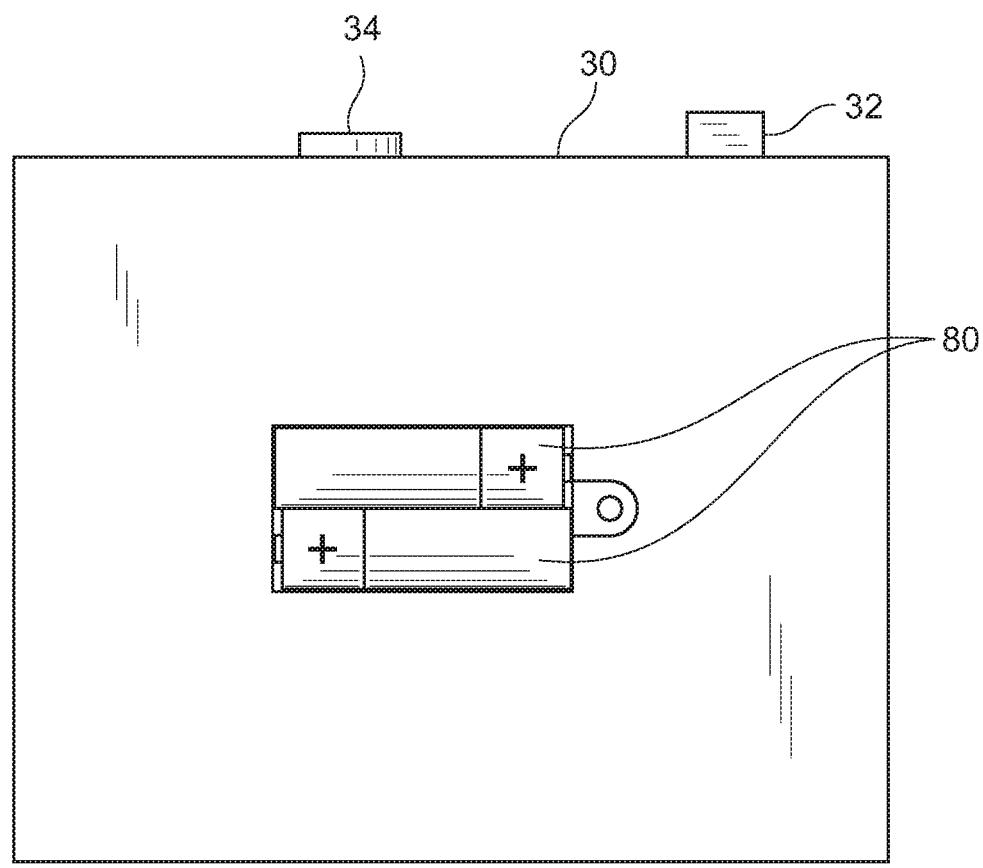
FIG. 11 is another bottom view of a bioluminescent tornado maker system in accordance with an example embodiment.

The toy tornado maker 10 may be battery powered—that is, both the air pump 42 and the electric motor 40 may be powered by batteries 80, under the control of circuitry within or mounted on the base 30. Other embodiments, such as those with a power supply that uses household current, are also possible. The system 10 may, for example, be powered by four AA batteries 80, as shown in FIGS. 9 and 11, and may be accessed or changed by opening door 37 in the bottom of the base, as shown in FIGS. 10 and 11.

C. Transparent Vessel

Figure 5:
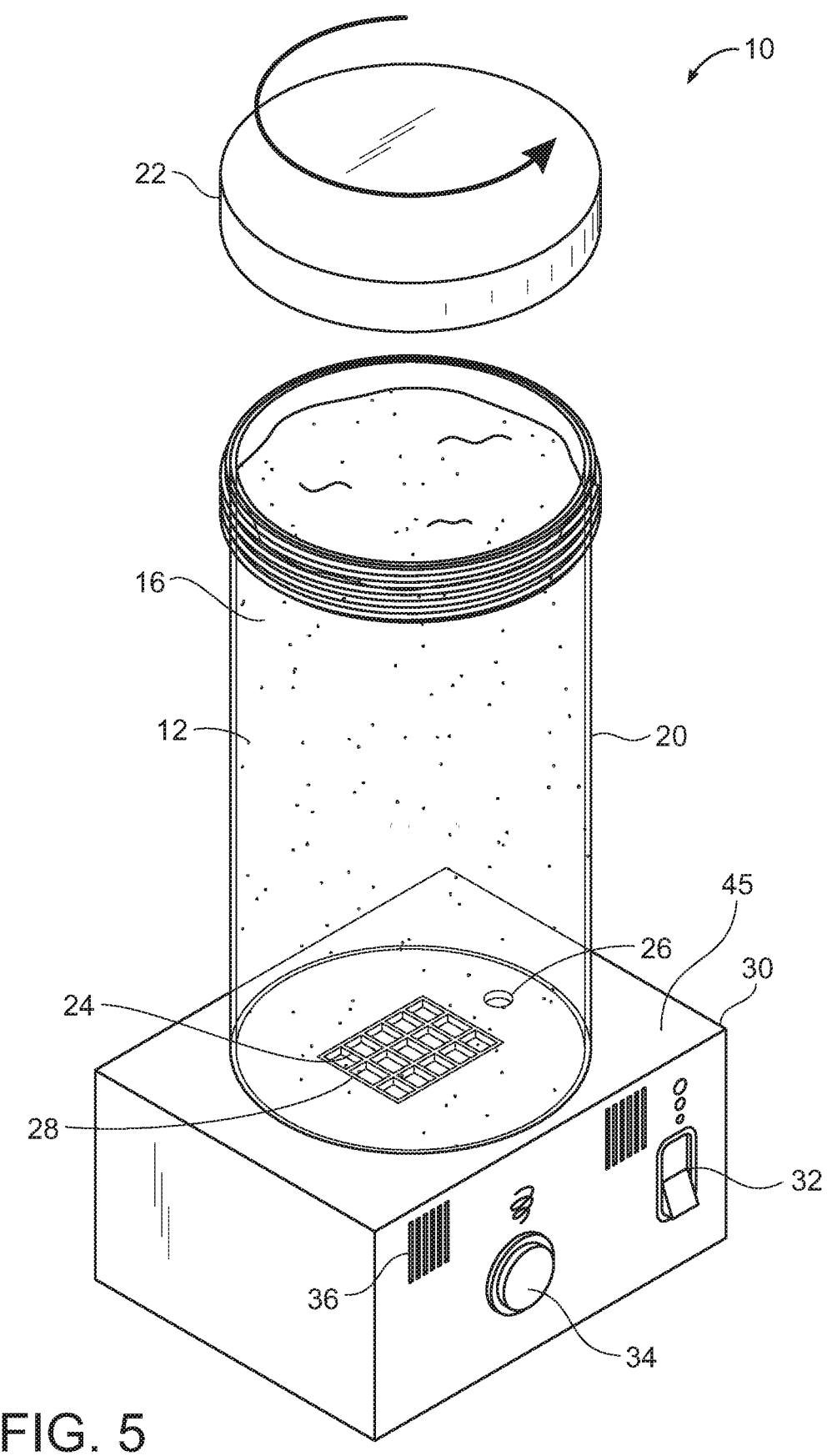
FIG. 5 is another perspective view of a bioluminescent tornado maker system in accordance with an example embodiment.

Example embodiments of the bioluminescent tornado maker system 10 may also include a transparent vessel 20, which, as shown, may be cylindrical, although other shapes are possible too. The vessel 20 may have a screw-on top 22, as best shown, for example, in FIG. 5. The removable top 22 allows for necessary ingredients to be added to the vessel 20. The main ingredients are of course a liquid medium 16, and the bioluminescent organisms 12. The liquid 16 may be or include salt water, since the bioluminescent organisms 12, which may be dinoflagellates, are salt water creatures. The liquid medium 16 may also contain or be fortified with phosphorous and nitrogen, as well as algae-type nutrients in which the bioluminescent organisms 12 can grow and thrive.

As discussed, the transparent vessel 20 is sealingly coupled or connected to the base 30, and the top or upper surface 45 of the base may serve as the bottom of the vessel 20 to contain the liquid medium within the vessel. Due to its transparency, the vessel 20 enables users to see the "tornado" generated by the toy, and to also see it glowing when used in the dark, as shown in FIG. 1.

D. Kit

Figure 6:
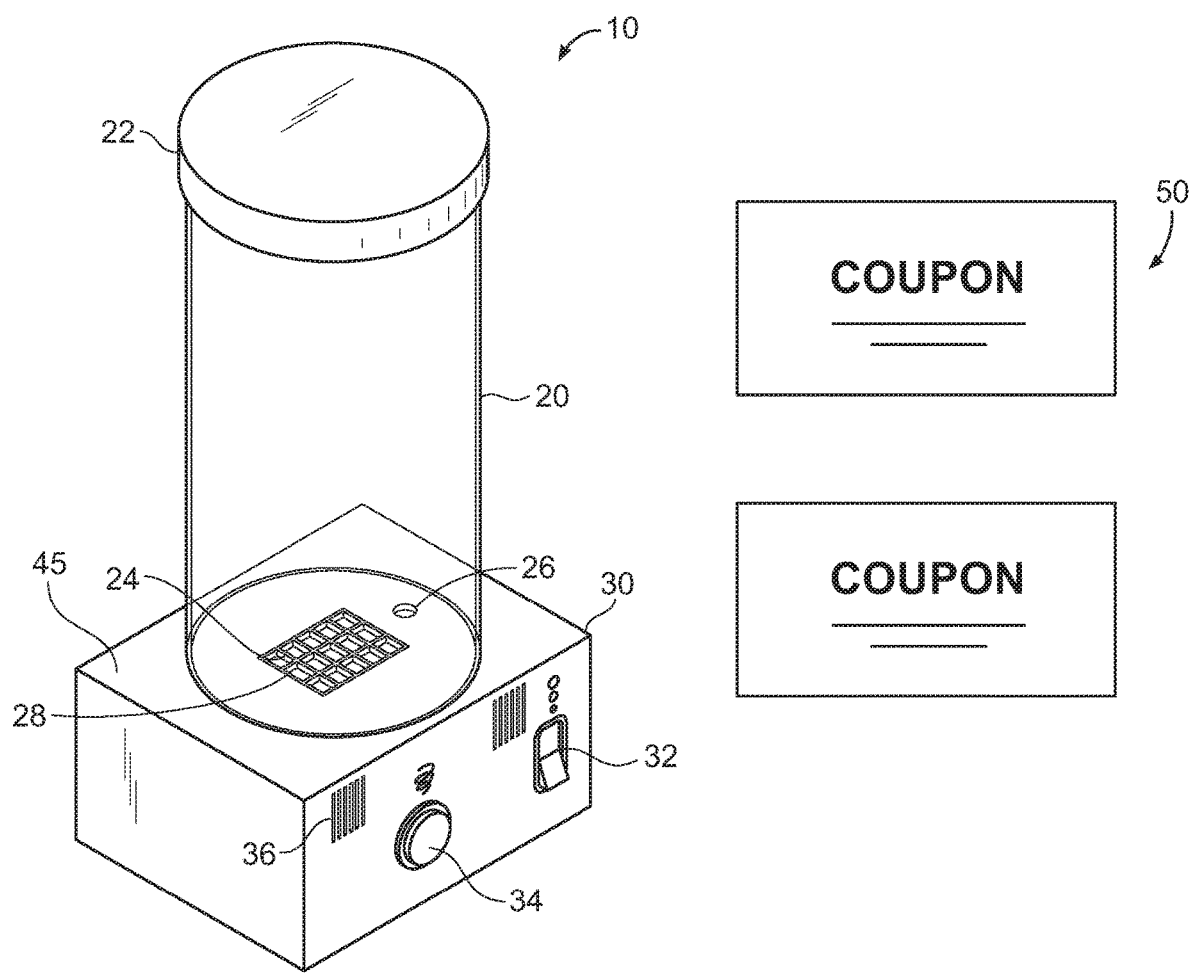
FIG. 6 is a perspective view of kit contents for a bioluminescent tornado maker system in accordance with an example embodiment.
Figure 7:
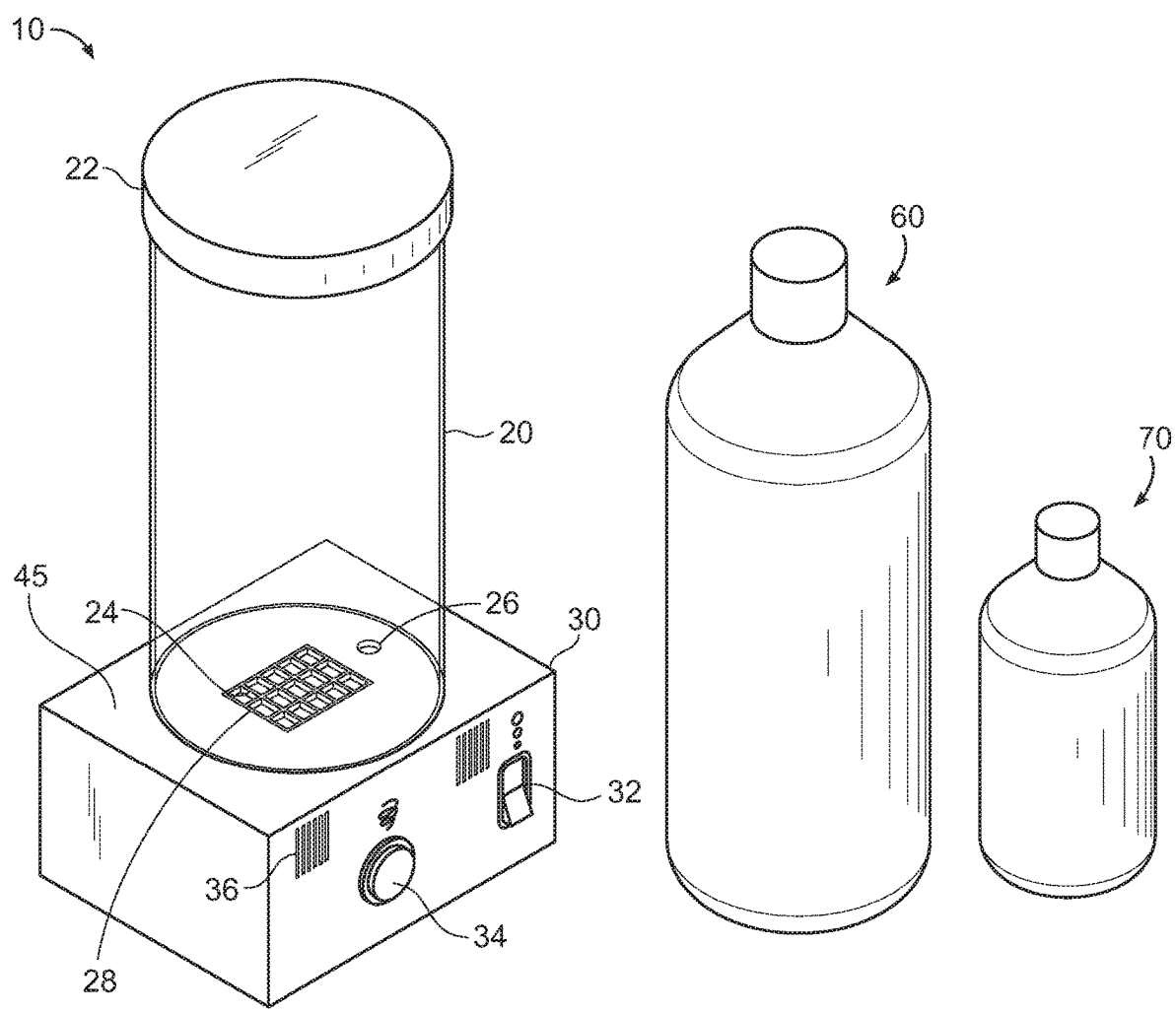
FIG. 7 is another perspective view of kit contents for a bioluminescent tornado maker system in accordance with an example embodiment.

The tornado maker system 10 may be sold in stores or online for delivery in the form of a kit, with most everything needed by the user. The items included in the kit are shown in FIG. 6, and include the tornado maker 10, as well as coupons 50, which a purchaser may use to send in to a seller for the liquid medium in a container 60, and the dinoflagellates or "dinos" in a container 70, to be shipped to the user. The cost of these ingredients may be included in the purchase price of the toy so that a user can simply go online and enter an address and a coupon code in order to have the medium and the dinos sent. Thus, the full kit, including bioluminescent organisms 12 and medium 16, in containers 60 and 70, are shown in FIG. 7.

E. Operation of Preferred Embodiment

Figure 8:
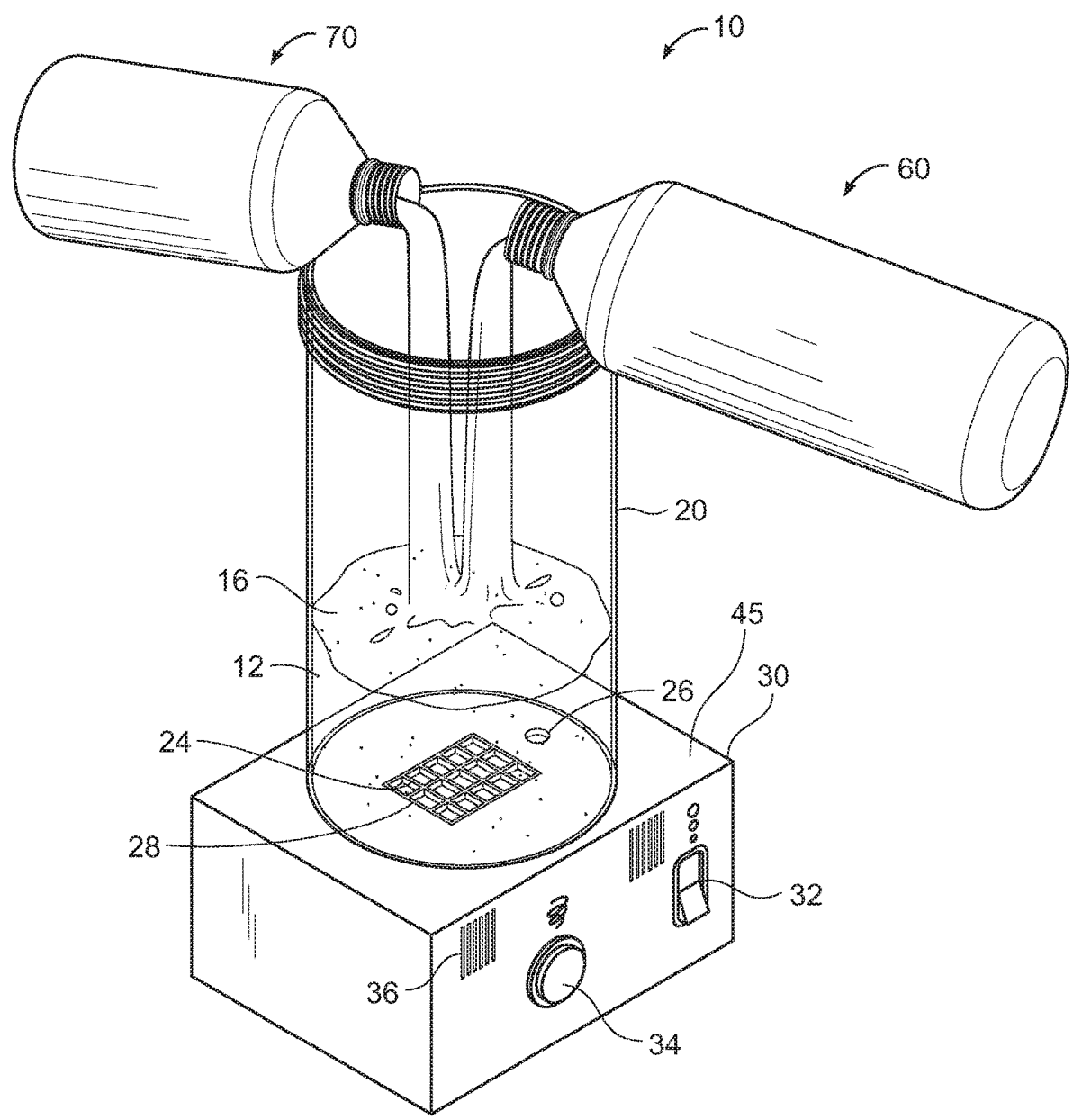
FIG. 8 is another perspective view of a bioluminescent tornado maker system in accordance with an example embodiment.

Once a user purchases the kit, they will use the two coupons 50 included with the kit to have the medium, shown by container 60, and the bioluminescent organisms, shown by container 70, shipped to them. Once these are received, the user simply unscrews the top 22 of transparent vessel 20 and pours the liquid 16 and the bioluminescent organisms 12 into the vessel, as shown in FIG. 8. Then the top is screwed back on. During the day, the tornado maker 10 may be exposed to sunlight, which is beneficial to the bioluminescent organisms.

The user may turn on switch 32 to operate the pump at any time, which will create a pleasing stream of bubbles that will rise to the top of the vessel 20, from orifice 26. When desired, the user may push the "tornado" button 34, which will activate the motor 40 and impeller 41, creating a tornado, which is a visible vortex within the vessel 20. Due to the presence of the bioluminescent organisms 12, the liquid, and the tornado, will emit visible bright blue flashes due to the mechanical disturbance, and the tornado will glow in the dark. If the pump has been activated, the tornado will also include bubbles 14. Typically, the glow from the dinos will last from a few seconds to a few minutes.

In addition to creating a pleasing visual effect, the pump 42 provides oxygen to the liquid medium, which can help the bioluminescent organisms 12 stay healthy. Further, the tornado maker can also be used as a desktop aquarium for fish or other animals, although in that case, it would not be recommended to turn the tornado feature on.

Unless otherwise defined, all technical and scientific terms used herein have the same meaning as commonly understood by one of ordinary skill in the art to which this invention belongs. Although methods and materials similar to or equivalent to those described herein can be used in the practice or testing of the bioluminescent tornado maker system, suitable methods and materials are described above. All publications, patent applications, patents, and other references mentioned herein are incorporated by reference in their entirety to the extent allowed by applicable law and regulations. The bioluminescent tornado maker system may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

What is claimed is:

1. A bioluminescent tornado maker, comprising:
   a transparent vessel;
   a liquid disposed within the transparent vessel, wherein the liquid comprises salt water and bioluminescent organisms;
   an impeller in contact with the liquid such that a rotation of the impeller causes a flow of the liquid;
   wherein the flow of the liquid creates a disturbance that causes the bioluminescent organisms to emit a visible light; and
   an air pump coupled to the transparent vessel, wherein the air pump creates air bubbles in the liquid.

2. The bioluminescent tornado maker of claim 1, wherein the flow of the liquid is a rotational flow.

3. The bioluminescent tornado maker of claim 2, wherein the flow of the liquid creates a visible vortex within the transparent vessel.

4. The bioluminescent tornado maker of claim 1, further comprising a base sealingly coupled to the transparent vessel, wherein the impeller is mounted in the base.

5. The bioluminescent tornado maker of claim 4, further comprising an electric motor mounted within the base, the electric motor coupled to the impeller such that the electric motor rotates the impeller when energized.

6. The bioluminescent tornado maker of claim 5, wherein the electric motor is energized for a limited time by a time-delay circuit.

7. The bioluminescent tornado maker of claim 1, further comprising a base sealingly coupled to the transparent vessel, wherein the electric motor is mounted in the base.

8. The bioluminescent tornado maker of claim 1, wherein the flow of the liquid creates a visible vortex within the transparent vessel, and wherein the visible vortex comprises air bubbles.

9. The bioluminescent tornado maker of claim 1, further comprising a base sealingly coupled to the transparent vessel.

10. The bioluminescent tornado maker of claim 9, further comprising an electric motor mounted within the base, the electric motor coupled to the impeller such that the electric motor rotates the impeller when energized.

11. The bioluminescent tornado maker of claim 10, wherein the electric motor is energized for a limited time by a time-delay circuit.

12. The bioluminescent tornado maker of claim 11, wherein the flow of the liquid creates a visible vortex within the transparent vessel, and wherein the visible vortex comprises air bubbles.

13. The bioluminescent tornado maker of claim 11, wherein the air pump is mounted within the base.

14. The bioluminescent tornado maker of claim 13, wherein the flow of the liquid creates a visible vortex within the transparent vessel, and wherein the visible vortex comprises air bubbles.

15. A bioluminescent tornado maker, comprising:
    a transparent vessel;

a liquid disposed within the transparent vessel, wherein the liquid comprises salt water and bioluminescent organisms;

an impeller in contact with the liquid such that a rotation of the impeller causes a flow of the liquid;

wherein the flow of the liquid creates a disturbance that causes the bioluminescent organisms to emit a visible light;

a base sealingly coupled to the transparent vessel, wherein the impeller is mounted in the base; and an electric motor mounted within the base, the electric motor coupled to the impeller such that the electric motor rotates the impeller when energized;

wherein the electric motor is energized for a limited time by a time-delay circuit.

16. The bioluminescent tornado maker of claim 15, wherein the flow of the liquid is a rotational flow that creates a visible vortex within the transparent vessel.

17. The bioluminescent tornado maker of claim 15, wherein the flow of the liquid creates a visible vortex within the transparent vessel, and wherein the visible vortex comprises air bubbles.

18. The bioluminescent tornado maker of claim 17, including an air pump mounted within the base that generates the air bubbles.

19. The bioluminescent tornado maker of claim 15, including an air pump mounted within the base.

20. A bioluminescent tornado maker, comprising:

a transparent vessel;

a liquid disposed within the transparent vessel, wherein the liquid comprises salt water and bioluminescent organisms;

an impeller in contact with the liquid such that a rotation of the impeller causes a flow of the liquid;

wherein the flow of the liquid creates a disturbance that causes the bioluminescent organisms to emit a visible light; and an air pump coupled to the transparent vessel, wherein the air pump creates air bubbles in the liquid;

wherein the flow of the liquid is a rotational flow;

wherein the flow of the liquid creates a visible vortex within the transparent vessel;

a base sealingly coupled to the transparent vessel, wherein the impeller is mounted in the base;

an electric motor mounted within the base, the electric motor coupled to the impeller such that the electric motor rotates the impeller when energized;

wherein the visible vortex comprises the air bubbles created by the air pump;

wherein the air pump is mounted within the base.

* * * * *